United States Patent
Hudson

(10) Patent No.: US 10,849,830 B2
(45) Date of Patent: Dec. 1, 2020

(54) FLOW DETECTION SYSTEM FOR FLOW CONTROL APPARATUS

(71) Applicant: KPR U.S., LLC, Mansfield, MA (US)

(72) Inventor: Joseph Hudson, O'Fallon, MO (US)

(73) Assignee: KPR U.S., LLC, Mansfield, MA (US)

(*) Notice: Subject to any disclaimer, the term of this patent is extended or adjusted under 35 U.S.C. 154(b) by 1103 days.

(21) Appl. No.: 14/807,495

(22) Filed: Jul. 23, 2015

(65) Prior Publication Data

US 2016/0022546 A1   Jan. 28, 2016

Related U.S. Application Data

(60) Provisional application No. 62/028,970, filed on Jul. 25, 2014.

(51) Int. Cl.
*A61M 5/168* (2006.01)
*A61M 5/142* (2006.01)
(Continued)

(52) U.S. Cl.
CPC ....... *A61J 15/0076* (2015.05); *A61J 15/0088* (2015.05); *A61M 5/14232* (2013.01);
(Continued)

(58) Field of Classification Search
None
See application file for complete search history.

(56) References Cited

U.S. PATENT DOCUMENTS

| 4,210,138 A | 7/1980 | Jess et al. |
| 4,394,862 A | 7/1983 | Shim |

(Continued)

FOREIGN PATENT DOCUMENTS

| EP | 0315312 A1 | 5/1989 |
| EP | 2468324 A1 | 6/2012 |

(Continued)

OTHER PUBLICATIONS

International Preliminary Report on Patentability dated Oct. 21, 2016 in related International Application No. PCT/US2015/041696, 7 pages.
(Continued)

*Primary Examiner* — Rebecca E Eisenberg
*Assistant Examiner* — Weng Lee
(74) *Attorney, Agent, or Firm* — Arent Fox LLP

(57) ABSTRACT

A flow control apparatus and method for accurate detection of occlusion conditions in a feeding set. A sensor is arranged with respect to a pumping device to produce a signal indicative of pressure in the feeding set. A control circuit that may receive the sensor signal from the sensor indicative of the pressure in the feeding set may also control operation of the pumping device. The control circuit is configured to operate the pumping device in an operational state, and in a reset state subsequent to the operational state in which the pumping device does not produce a pumping action and the pumping device is moved to a position in which the pumping device does not block the feeding set to permit fluid flow in a backflow direction opposite to the patient direction thereby relieving any built up pressure in the feeding set downstream of the pumping device.

24 Claims, 10 Drawing Sheets

(51) Int. Cl.
*A61J 15/00* (2006.01)
*G06F 19/00* (2018.01)

(52) U.S. Cl.
CPC ..... *A61M 5/16813* (2013.01); *G06F 19/3468* (2013.01); *A61M 2005/16863* (2013.01); *A61M 2205/3331* (2013.01); *A61M 2205/3334* (2013.01); *A61M 2205/3351* (2013.01); *A61M 2205/50* (2013.01); *A61M 2205/52* (2013.01)

(56) References Cited

U.S. PATENT DOCUMENTS

| | | | |
|---|---|---|---|
| 4,506,553 | A | 3/1985 | Bruce et al. |
| 5,514,102 | A | 5/1996 | Winterer et al. |
| 5,720,721 | A * | 2/1998 | Dumas .............. A61M 5/16854 604/118 |
| 5,827,223 | A * | 10/1998 | Butterfield ........ A61M 5/16859 604/65 |
| 5,906,589 | A | 5/1999 | Gordon et al. |
| 6,149,394 | A | 11/2000 | Allen |
| 7,092,797 | B2 * | 8/2006 | Gaines .............. A61M 5/14232 604/65 |
| 7,447,566 | B2 | 11/2008 | Knauper et al. |
| 7,621,893 | B2 | 11/2009 | Moberg et al. |
| 2005/0070871 | A1 * | 3/2005 | Lawton ............... A61M 1/0001 604/403 |
| 2010/0082011 | A1 | 4/2010 | Lewis et al. |
| 2010/0280486 | A1 | 11/2010 | Khair et al. |

FOREIGN PATENT DOCUMENTS

| | | |
|---|---|---|
| JP | 2005-240575 A | 9/2005 |
| WO | 9707843 A1 | 3/1997 |
| WO | 2005088132 A1 | 9/2005 |
| WO | 2010146579 A1 | 12/2010 |

OTHER PUBLICATIONS

Response filed Sep. 21, 2016 to Written Opinion dated Jun. 14, 2016 in related International Application No. PCT/US2015/041696, 21 pages.

International Search Report dated Oct. 20, 2015 in related application PCT/US2015/041696, 5 pages.

Written Opinion of the International Searching Authority dated Oct. 20, 2015 in related application PCT/US2015/041696, 5 pages.

Written Opinion of the International Preliminary Examining Authority dated Jun. 14, 2016 in related Application No. PCT/US2015/041696, 5 pages.

English Translation of Notice of Reasons for Rejection for Japanese Application No. 2017-503837, dated Jul. 11, 2019, 3 pages.

Examination Report for Australian Application No. 2015292569, dated Jun. 16, 2019, 3 pages.

Examination Report for European Patent Application No. 15747897.5, dated Apr. 4, 2019, 5 pages.

\* cited by examiner

FLOW DETECTION SYSTEM FOR FLOW CONTROL APPARATUS

CROSS-REFERENCE TO RELATED APPLICATION

This application claims the benefit of priority to U.S. Patent Application Ser. No. 62/028,970, titled FLOW DETECTION SYSTEM FOR FLOW CONTROL APPARATUS, filed on Jul. 25, 2014, which is incorporated herein by reference in its entirety for all purposes.

FIELD OF THE INVENTION

The present invention generally relates to a flow control apparatus capable of detecting a flow condition in a tube set mounted on the apparatus.

BACKGROUND OF THE INVENTION

Administering fluids containing medicine or nutrition on an ongoing basis in precise quantities to a patient is known in the art. Typically, nutritional fluid is delivered to the patient by an administration feeding set including a source of nutritional liquid that is loaded to a flow control apparatus, such as a pump that delivers fluid to the patient.

A flow control apparatus of the prior art may also be capable of monitoring and detecting fluid flow conditions that can occur within the loaded administration feeding set during operation of the flow control apparatus. One such flow condition is an occlusion in the feeding set. The presence of an occlusion prevents nutritional liquid from being delivered to the patient and can damage the feeding set and flow control apparatus. Generally, existing flow monitoring systems that are capable of monitoring and detecting flow conditions perform rely exclusively on conditions detected while the flow control apparatus is operating to deliver nutritional liquid. However, it can difficult for the system to distinguish between abnormal and normal flow conditions in the feeding set while the apparatus is operating to deliver fluid through the feeding set.

SUMMARY OF THE INVENTION

In a first aspect, a flow control apparatus adapted for loading a feeding set generally comprises a housing capable of receiving at least a portion of the feeding set, and a pumping device for contacting the feeding set when the feeding set is received by the housing so the pumping device acts on the feeding set to produce fluid flow in the feeding set for delivery of fluid in a patient direction to a patient. A sensor is arranged with respect to the pumping device to produce a signal indicative of pressure in the feeding set when the feeding set is loaded on the apparatus for determining a flow condition in the feeding set. A control circuit in communication with the sensor receives the sensor signal from the sensor indicative of the pressure in the feeding set. The control circuit is in communication with the pumping device to control operation of the pumping device. The control circuit is configured to operate the pumping device in an operational state in which the pumping device is adapted to contact the feeding set to produce a peristaltic pumping action of fluid in the patient direction through the feeding set, and in a reset state subsequent to the operational state in which the pumping device does not produce a peristaltic pumping action and the pumping device is moved to a position in which the pumping device does not block the feeding set to permit fluid flow in a backflow direction opposite to the patient direction thereby relieving any built up pressure in the feeding set downstream of the pumping device. In some embodiments, the control circuit is adapted to control the pumping device in the reset state to move to a position that does not deform the feeding set that blocks flow of fluid through the feeding set. In certain embodiments, the pumping device comprises an actuator and pumping members operatively connected to the actuator for being moved by the actuator to repeatedly deform and relieve deformation of the feeding set for producing fluid flow in the feeding set in the patient direction. In some cases, the control circuit in the reset state of the pumping device causes the pumping members to move to relieve deformation of the feeding set. In some cases, the pumping device comprises a rotor operatively connected to the actuator for being driven in rotation by the actuator. In some cases, the pumping members comprise rollers mounted on the rotor. In certain embodiments, the control circuit includes a memory and is configured to determine a first occlusion condition by comparing a baseline sensor signal acquired from the sensor prior to the operational state of the pumping device and stored in the memory with a peak sensor signal acquired during the reset state of the pumping device and stored in the memory. In some embodiments, the control circuit is configured to operate the pumping device in a hold state, typically subsequent to the operational state and, in some cases, prior to the reset state, in which the pumping device does not produce a peristaltic pumping action and the pumping device is moved to a position in which the pumping device deforms the feeding set that blocks fluid flow in a backflow direction. In certain embodiments, the control circuit is configured to indicate that an occlusion is present in the feeding set only if said reset and hold conditions are found to indicate the presence of an occlusion in plural cycles of operation of the flow control apparatus where one cycle of operation includes the sequential operation of the pumping device in the operational state, the hold state and then the reset state. In some embodiments, the sensor comprises an ultrasonic sensor including a receiver and an ultrasonic transmitter. Typically, the transmitter is configured to transmit an ultrasonic signal through a downstream side of the feeding set to the receiver for determining the downstream flow condition of the feeding set when the feeding set is loaded on the apparatus.

In a second aspect, a flow control apparatus adapted to load a feeding set generally comprises a housing capable of receiving at least a portion of the feeding set, and a pumping device for contacting the feeding set when the feeding set is received by the housing so the pumping device acts on the feeding set to produce fluid flow in the feeding set in a patient direction for delivery of fluid to a patient. A sensor is arranged with respect to the pumping device to produce a signal indicative of pressure in the feeding set when the feeding set is loaded on the apparatus for determining a flow condition in the feeding set. A control circuit in communication with the sensor receives the sensor signal from the sensor indicative of the pressure in the feeding set. The control circuit is in communication with the pumping device to control operation of the pumping device. The control circuit is configured to operate the pumping device in an operational state in which the pumping device is adapted to contact the feeding set to produce a peristaltic pumping action of fluid in the patient direction through the feeding set, in a hold state in which the pumping device does not produce a peristaltic pumping action and blocks fluid flow in the feeding set in a backflow direction opposite to the patient direction. In some embodiments, the control circuit is adapted to control the pumping device in the hold state to deform the set to block flow of fluid in the backflow direction. In certain embodiments, the control circuit comprises a memory and is configured to store a peak sensor signal from the operational state of the pumping device in the memory, and configured to store the dissipation sensor signal from the hold state of the pumping device in the memory. In some embodiments, the control circuit is configured to delay for a predetermined period following onset of the hold state before acquiring the dissipation sensor signal to be stored in the memory. In certain embodiments, the control circuit is configured to compare the peak sensor signal with the dissipation sensor signal. In some embodiments, the control circuit is configured to find that a first occlusion condition is satisfied if the dissipation sensor signal is not less than the peak sensor signal by more than a dissipation threshold amount. In certain embodiments, the control circuit is configured to compare the dissipation sensor signal with a baseline sensor signal taken in a reset state in which the pumping device does not produce a peristaltic pumping action and the pumping device is moved to a position in which the pumping device does not block the feeding set to permit fluid flow in the backflow direction and stored in the memory. In some embodiments, the control circuit is configured to compare the baseline sensor signal with the peak sensor signal. In certain embodiments, the control circuit is configured to indicate that an occlusion is present in the feeding set if the following conditions are found: (1) the peak sensor signal is greater than the baseline sensor signal by more than the pumping threshold amount; (2) the dissipation sensor signal is greater than the baseline sensor signal by more than a baseline threshold amount, and (3) the dissipation sensor signal is not less than the peak sensor signal by more than a dissipation threshold amount. In some embodiments, the control circuit is configured to indicate that an occlusion is present in the feeding set only if said conditions are found in plural cycles of operation of the flow control apparatus. One cycle of operation includes the sequential operation of the pumping device in the operational state, the hold state and then the reset state.

In a third aspect, a method of operating a flow control apparatus including a pumping device for detecting occlusions in fluid flow in a pump set acted upon by the flow control apparatus. The method generally comprises operating the pumping device using the control circuit in an operational state to repeatedly deform the pump set for pumping fluid in the pump set. Operation of the pumping device is halted using the control circuit. Then the pumping device is moved using the control circuit to a position in which the pumping device does not block the feeding set to permit fluid flow in a backflow direction opposite to a pumping direction in which fluid in the pump set is pumped by the pumping device in the operational state. In some embodiments, the method further comprises operating the pumping device using the control circuit in a hold state in which the pumping device does not pump fluid in the pump set and blocks flow of fluid in the pump set in the backflow direction. In certain embodiments, the method further comprises storing in a memory associated with a control circuit a baseline sensor signal from a sensor positioned to detect pressure in the pump set prior to initiation of operation of the pumping device by the control circuit to pump fluid in the pump set. A peak sensor signal from the sensor acquired during operation of the pumping device in the operational state is stored in the memory, as is a dissipation sensor signal from the sensor acquired during operation of the pumping device in the hold state. The control circuit compares the baseline sensor signal, the peak sensor signal and dissipation sensor signal with each other. The presence of an occlusion in the pump set is determined by the control circuit only if a condition is satisfied in which the dissipation sensor signal is less than the peak sensor signal by less than a dissipation threshold amount. In some embodiments, determining with the control circuit the presence of an occlusion in the pump set further comprises determining if the following conditions are also met: (1) determining using the control circuit that the peak sensor signal is greater than the baseline sensor signal by more than a pumping threshold amount, and (2) determining using the control circuit that the dissipation sensor signal is greater than the baseline sensor signal by more than a baseline threshold amount.

Other objects and features will be in part apparent and in part pointed out hereinafter.

BRIEF DESCRIPTION OF THE DRAWINGS

Corresponding reference characters indicate corresponding parts throughout the drawings.

DETAILED DESCRIPTION

Figure 1:
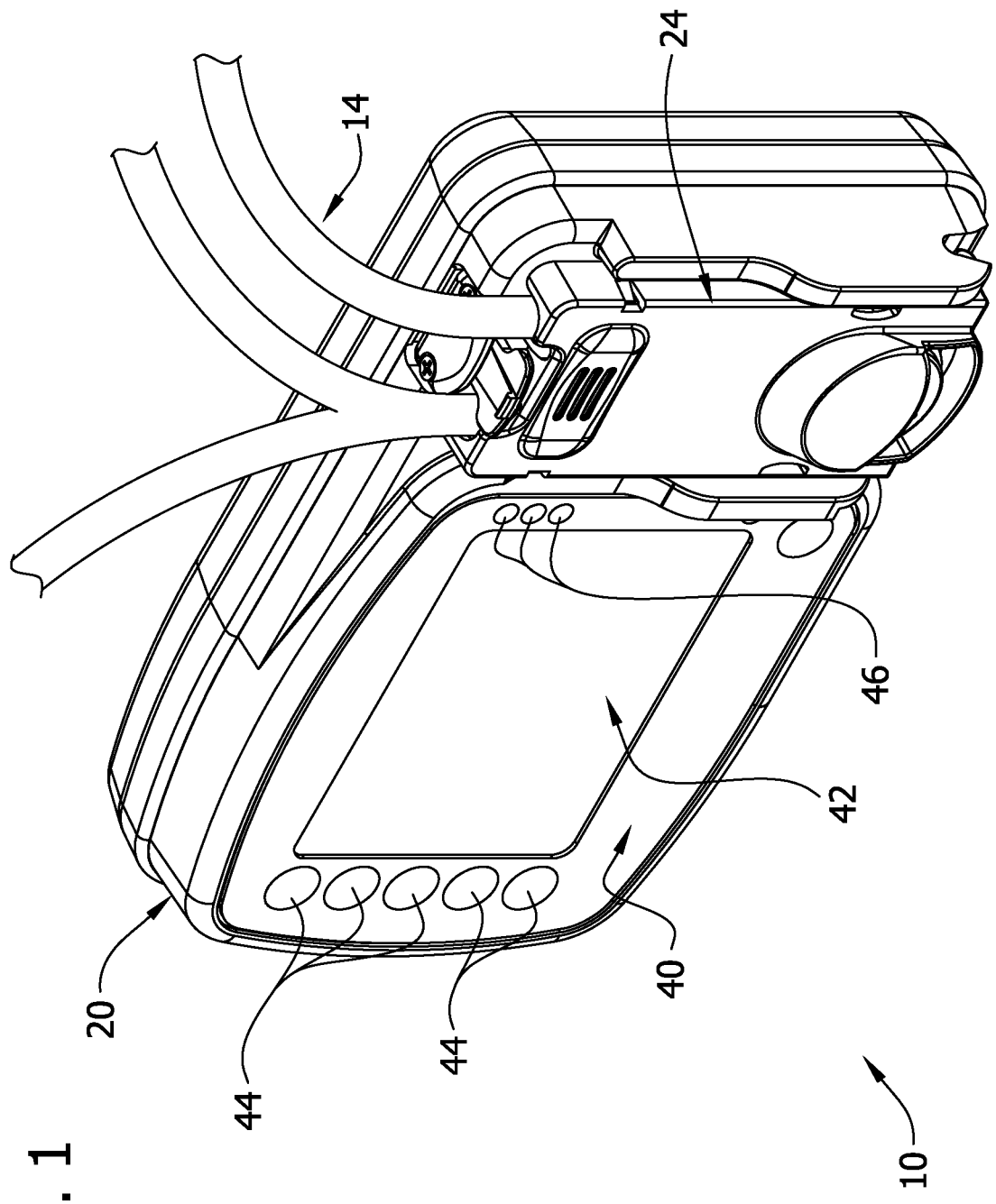
FIG. 1 is a perspective of an enteral feeding pump and a fragmentary portion of a feeding set received on the pump.
Figure 2:
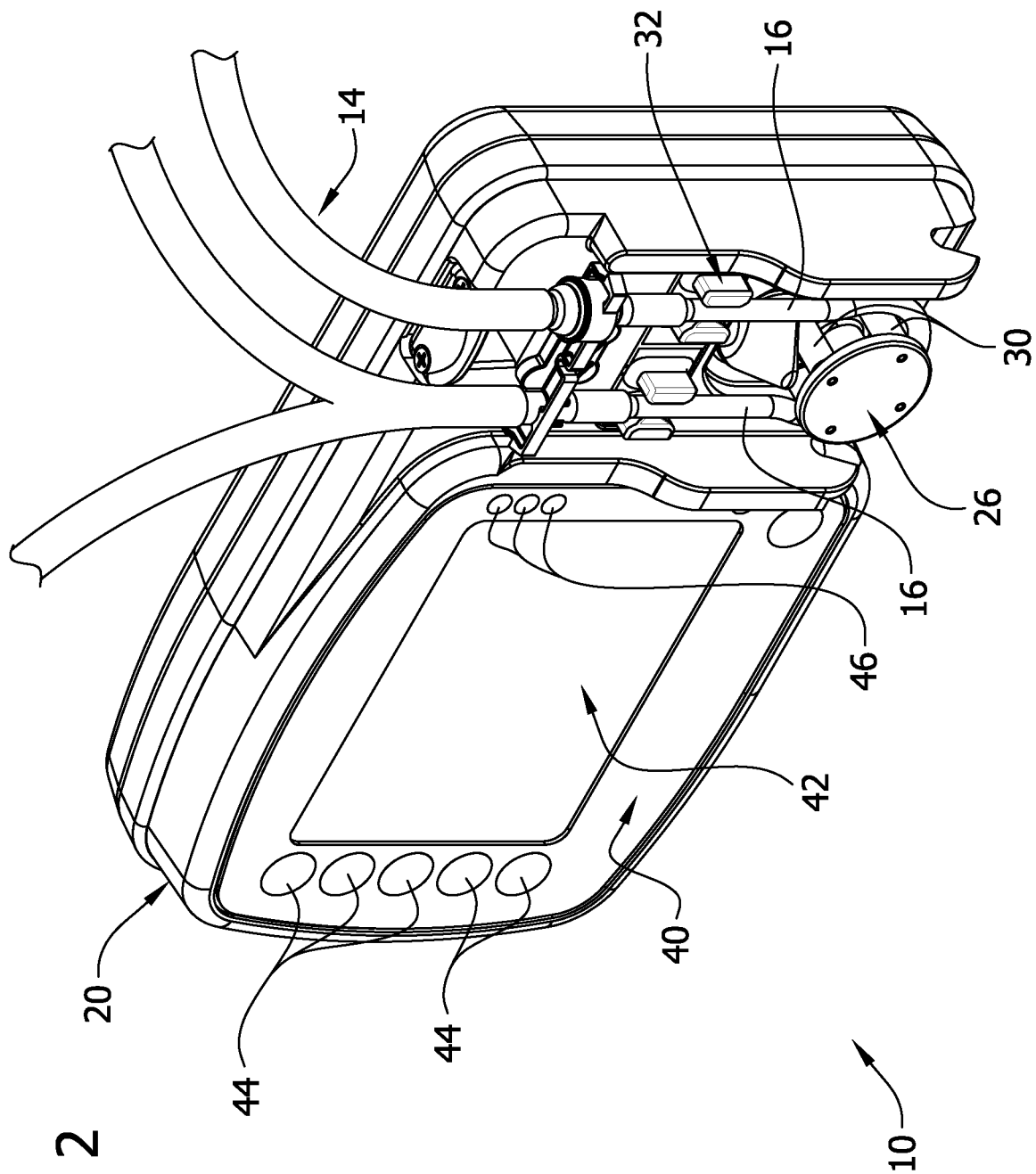
FIG. 2 is a perspective of FIG. 1 with a cassette housing of the feeding set removed.
Figure 3:
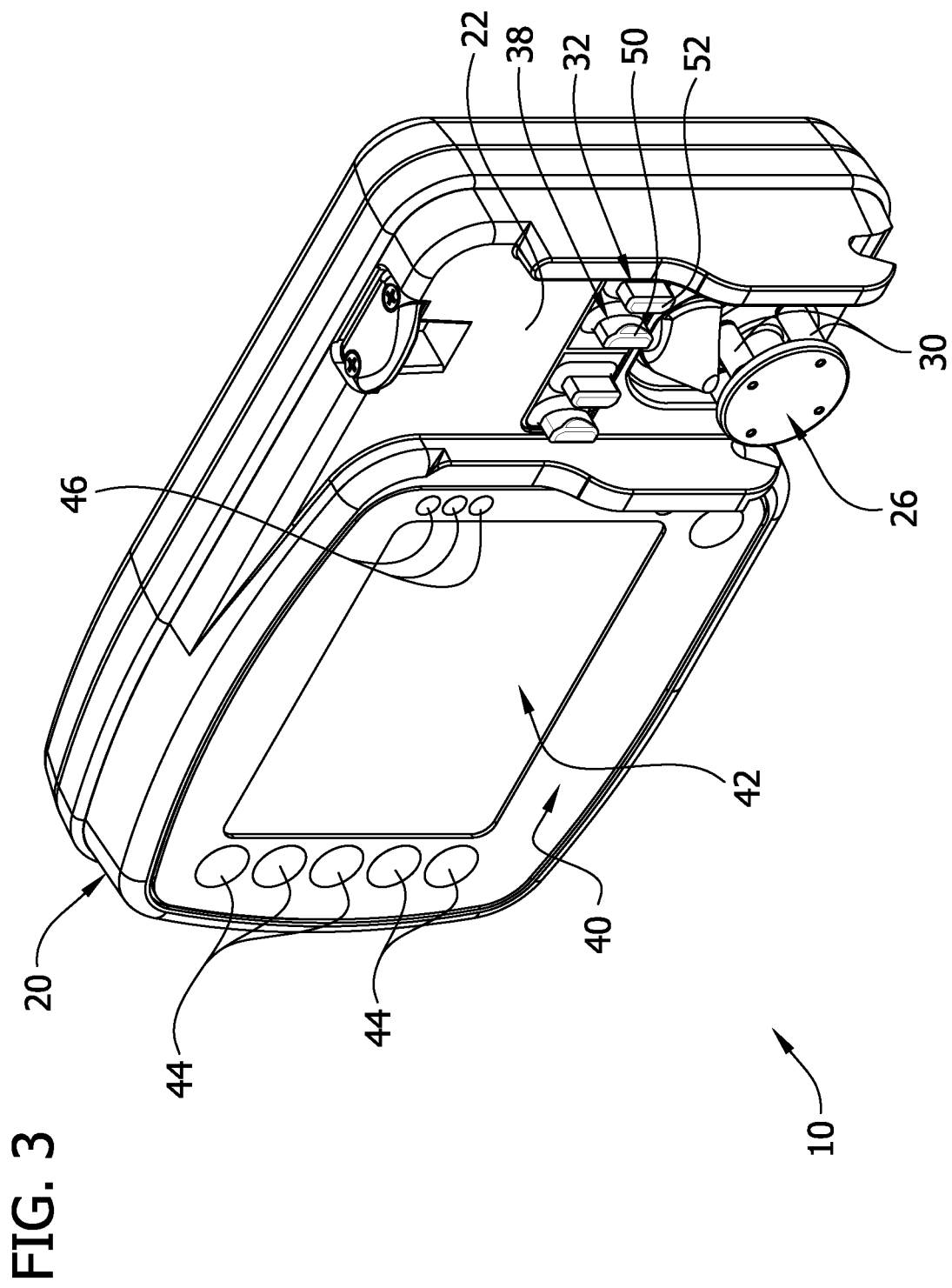
FIG. 3 is the perspective of FIG. 1 with the feeding set removed.

Referring to the drawings and in particular to FIGS. 1-3, an embodiment of a flow control apparatus is generally indicated at 10. The flow control apparatus may comprise a flow monitoring system 12 (FIG. 4) that is capable of detecting and identifying a flow condition present within a feeding set 14 loaded on the apparatus. The feeding set 14 may include tubing 16 that can be loaded on the flow control apparatus 10 for delivery of fluid to a patient. As used herein, the term "load" means that the tubing 16 is engaged with the flow control apparatus 10 so that the administration feeding set 14 is ready for operation with the flow control apparatus 10 to deliver fluid through the feeding set to a patient.

Figure 4:
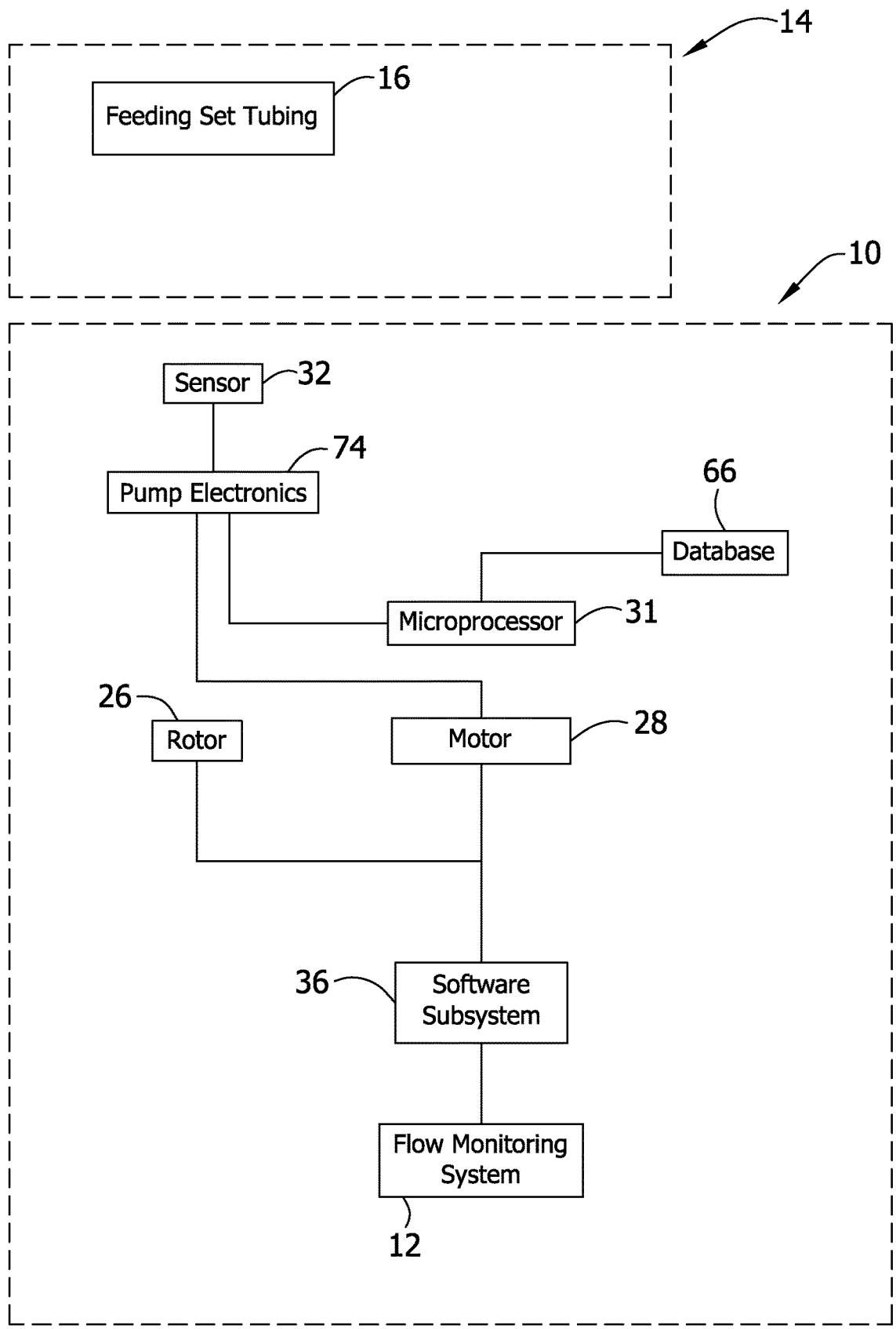
FIG. 4 is a block diagram illustrating elements of the flow control apparatus including a flow monitoring system.

The flow control apparatus 10 may comprise a housing 20 adapted for loading the feeding set 14 (broadly, "pump set") to the flow control apparatus 10. The flow control apparatus may comprise a recess 22 for receiving a cassette 24 of the feeding set 14 to load the feeding set on the flow control apparatus 10. Preferably, a means for driving fluid, such as a rotor 26, may be rotated by a motor 28 (FIG. 4). The rotor 26 includes rollers 30 (broadly, "pumping members") spaced around the rotor. The rollers 30 may be adapted to sequentially and repeatedly engage the tubing 16 so that the tubing can be compressed by the rotor when the feeding set 14 is loaded to the flow control apparatus 10 to produce fluid flow through the feeing set by peristaltic action.

As used herein, the portion of tubing 16 of the feeding set 14 leading to rotor 26 is termed "upstream," while the portion of tubing 16 leading away from rotor 26 is termed "downstream." Accordingly, rotation of rotor 26 compresses the tubing 16 to drive fluid (e.g., a nutritional liquid) in a patent direction from the upstream to the downstream side of the feeding set 14. As will be explained in greater detail below, rotation of the rotor 26 to compress the tubing 16 also generates positive pressure within the tubing when an occlusion is present in the tubing. In the illustrated embodiment, the motor 28 (broadly, "an actuator") and rotor 26 may be considered "a pumping device". However, other pumping devices (e.g., non-rotary devices) are envisioned. Moreover, although an exemplary feeding set 14 is shown, feeding sets of other configurations and other types of pump sets (not shown) can be used.

Referring to FIG. 4, the flow control apparatus 10 may further comprise a microprocessor 31 in communication association with a sensor 32. A software subsystem 36 may be operatively associated with the microprocessor 31 and operatively associated with the flow monitoring system 12 to provide a means for the flow control apparatus 10 to detect and identify a flow condition present in the feeding set 14. The sensor 32 may comprise an ultrasonic sensor for detecting a change in pressure in the downstream side of the feeding set 14.

The sensor 32 may be located on the housing 20 of the flow control apparatus 10 and positioned to detect pressure change in the downstream side of the feeding set 14. In the illustrated embodiment, the sensor 32 is positioned in recess 22 and is adapted to securely receive the tubing 16 therein when the feeding set 14 is loaded on the flow control apparatus 10. In order for the sensor 32 to detect the change in pressure in the tubing 16 of the feeding set 14, the tubing may be engaged and retained within sensor track 38 configured to receive the downstream side of the feeding set. Once the tubing 16 is engaged within the sensor track 38 and the remaining portions of the feeding set 14 are engaged with the apparatus 10, the flow monitoring system 12 may become operational.

Referring to FIG. 1, flow control apparatus 10 may further comprise a user interface 40 for interaction with the flow control apparatus 10. The apparatus may also have a display screen generally indicated at 42 on the front of the apparatus that is capable of displaying information about the status and operation of the pump. Buttons 44 on the side of the display screen 42 can be provided for use in controlling and obtaining information from the pump 1, and three light emitting diodes 46 can provide status information for the pump. A user interface may have configurations other than described herein without departing from the scope of the present invention.

Microprocessor 31 may control and manage the operation of the various components of the flow control apparatus 10. Preferably, the sensor 32 may comprise an ultrasonic transmitter 50 that transmits an ultrasonic signal through the downstream portion of the tubing 16 seated in the sensor track 38 to detect pressure changes in the downstream side of the feeding set 14 when the signal is received by a receiver 52. Upon receipt of the ultrasonic signal, receiver 52 may detect the pressure within the tubing 16 along sensor track 38 based on the characteristics of the ultrasonic signal received by the microprocessor 31. The ultrasonic signal may detect the presence or absence of fluid in the tubing to give a basic indication of the operational status of the flow control apparatus 10. The ultrasonic signal may be responsive to the pressure in the tubing 16 such that an increase in pressure in the tubing will produce an increase in amplitude of the signal. In particular, the compressing of the tubing 16 by the rotor 26 when an occlusion in the tubing is present may cause the tubing to swell and increase a coupling of the tubing to the sensor 32. Thus in one or embodiments, the coherence or the strength of the signal will increase with increased pressure on the downstream side of the feeding set 14. Conversely, a decrease in pressure in the tubing 16 may cause a decrease in the amplitude of the ultrasonic signal. The receiver 52 may then communicate with the microprocessor 31. Based on the characteristics of the received ultrasonic signal communicated to the microprocessor 31, the software subsystem 36 may determine whether fluid flow within the feeding set 14 is normal or if a flow abnormality exists. In the illustrated embodiment, the sensor 32 is disposed at the downstream side of the feeding set 14. However, the sensor 32 could be disposed at the upstream side of the feeding set 14. Also, other types of sensors for measuring pressure other than ultrasonic sensors can be used.

Figure 6:
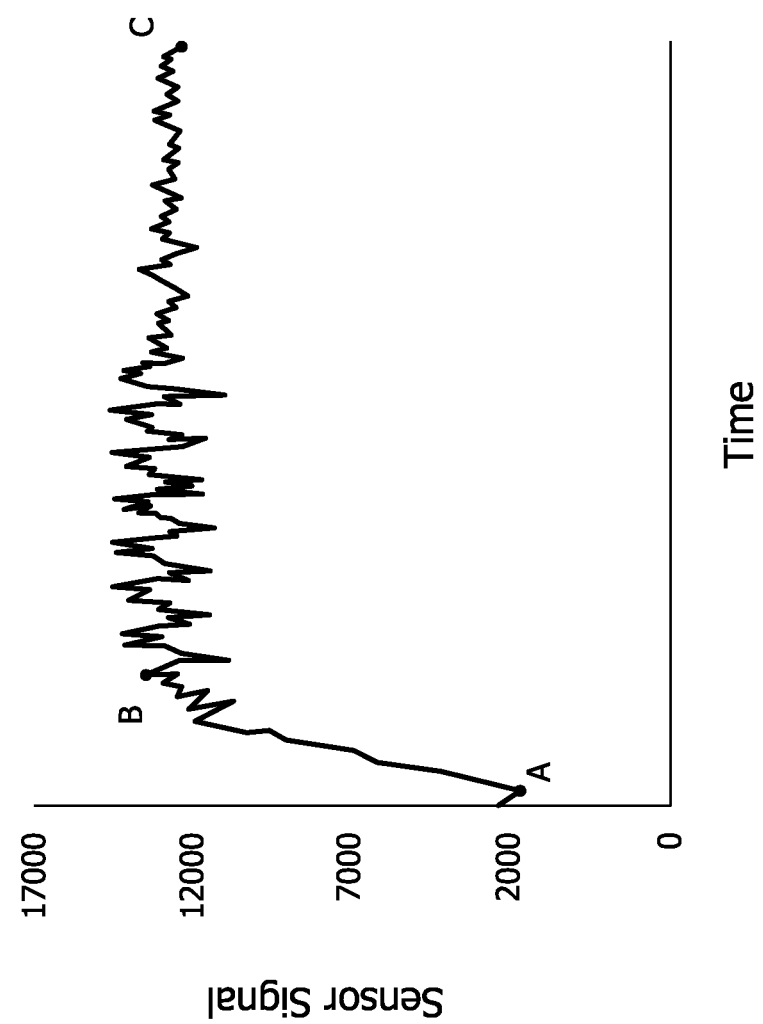
FIG. 6 is a graph illustrating signal strength over time for an occluded condition for a non-viscous fluid detected by a sensor of the flow monitoring system.
Figure 7:
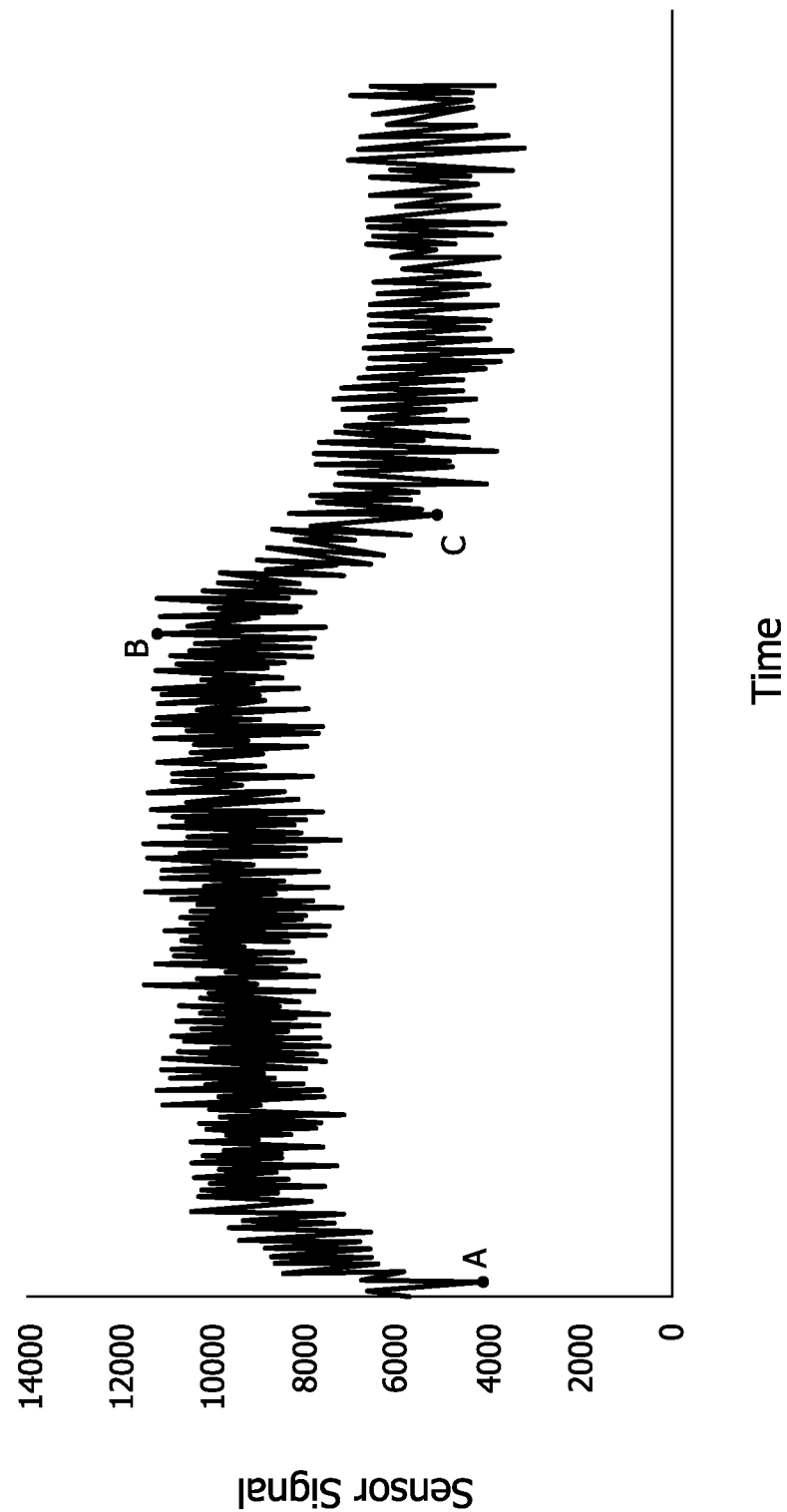
FIG. 7 is a graph illustrating signal strength over time for a non-occluded condition for a viscous fluid detected by the sensor of the flow monitoring system.

Software subsystem 36 may determine through a series of decision points and steps whether normal flow or abnormal flow conditions exist within tubing 16, and if an abnormal flow condition is detected, whether it is an occlusion or an artifact resulting from a normal flow condition that resembles an abnormal flow condition. A normal flow condition exists when there is no flow condition that would occlude or obstruct fluid flow in the downstream side of the feeding set 14. However, when viscous fluids are used, the pressure in the feeding set 14 may increase during otherwise normal flow conditions. Thus, a normal flow condition can appear to the sensor 32 to be an abnormal flow condition when a viscous fluid is used with the feeding set 14. In one embodiment, a pressure of between about 3 and about 5 psi is produced in the tubing 16 during non-occluded operation of the pumping device when a non-viscous fluid is used and a pressure of between about 1 and about 15 psi, e.g., in a range that is greater than about 5 psi to about 15 psi, is produced in the tubing 16 during non-occluded operation of the pumping device when a viscous fluid is used. Reference is made to FIG. 6 illustrating a signal output from the sensor 32 in an occluded condition for a non-viscous fluid, and FIG. 7 illustrating a signal output for the sensor in a non-occluded condition for a viscous fluid. As can be seen in the figures, the rise in signal amplitude is similar for the two flow conditions. For the purpose of discussion, a non-viscous fluid has a viscosity of less than about 75 cP, and a viscous fluid has a viscosity greater than or equal to about 75 cP.

Figure 5:
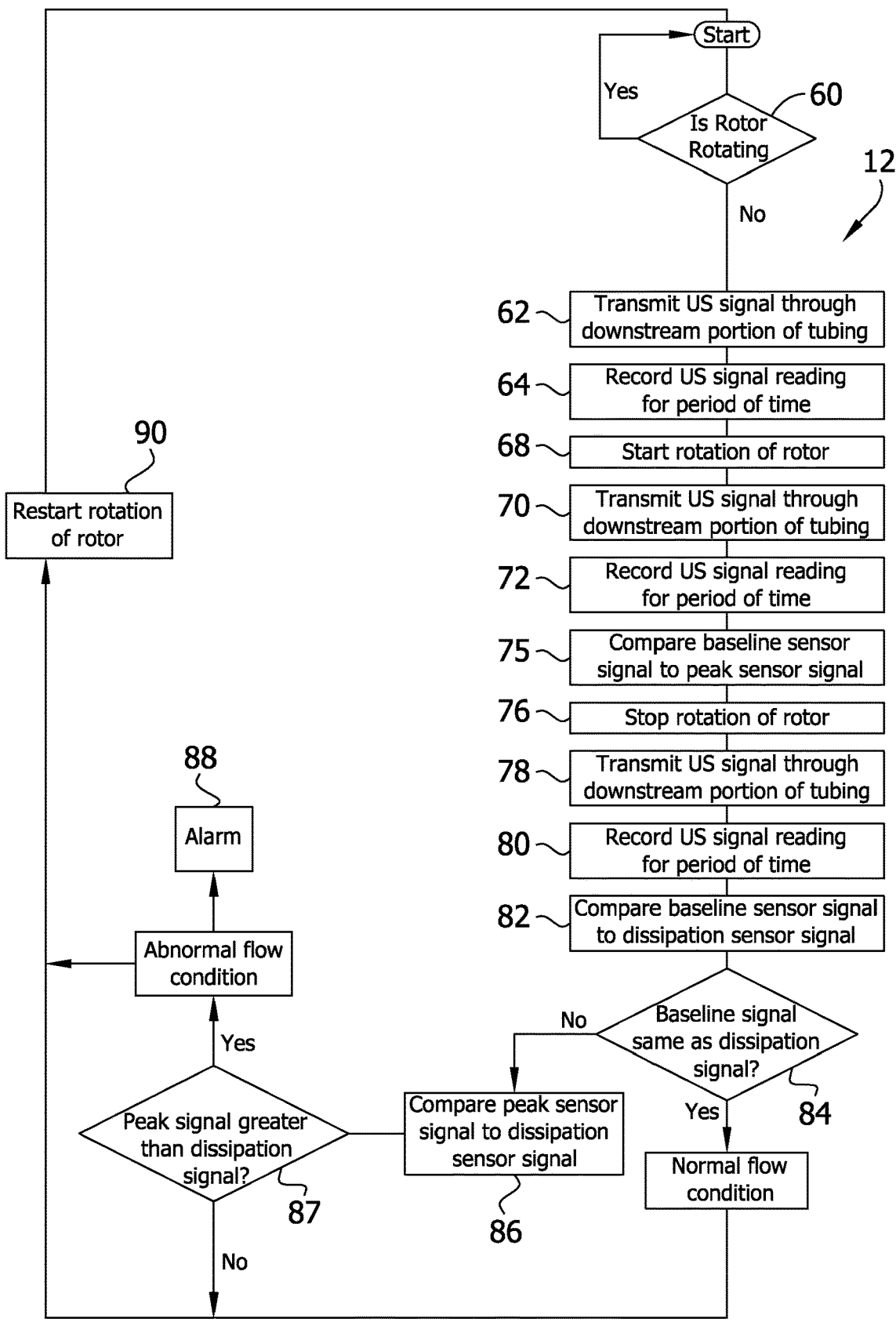
FIG. 5 is a flow chart of the flow monitoring system.
Figure 8:
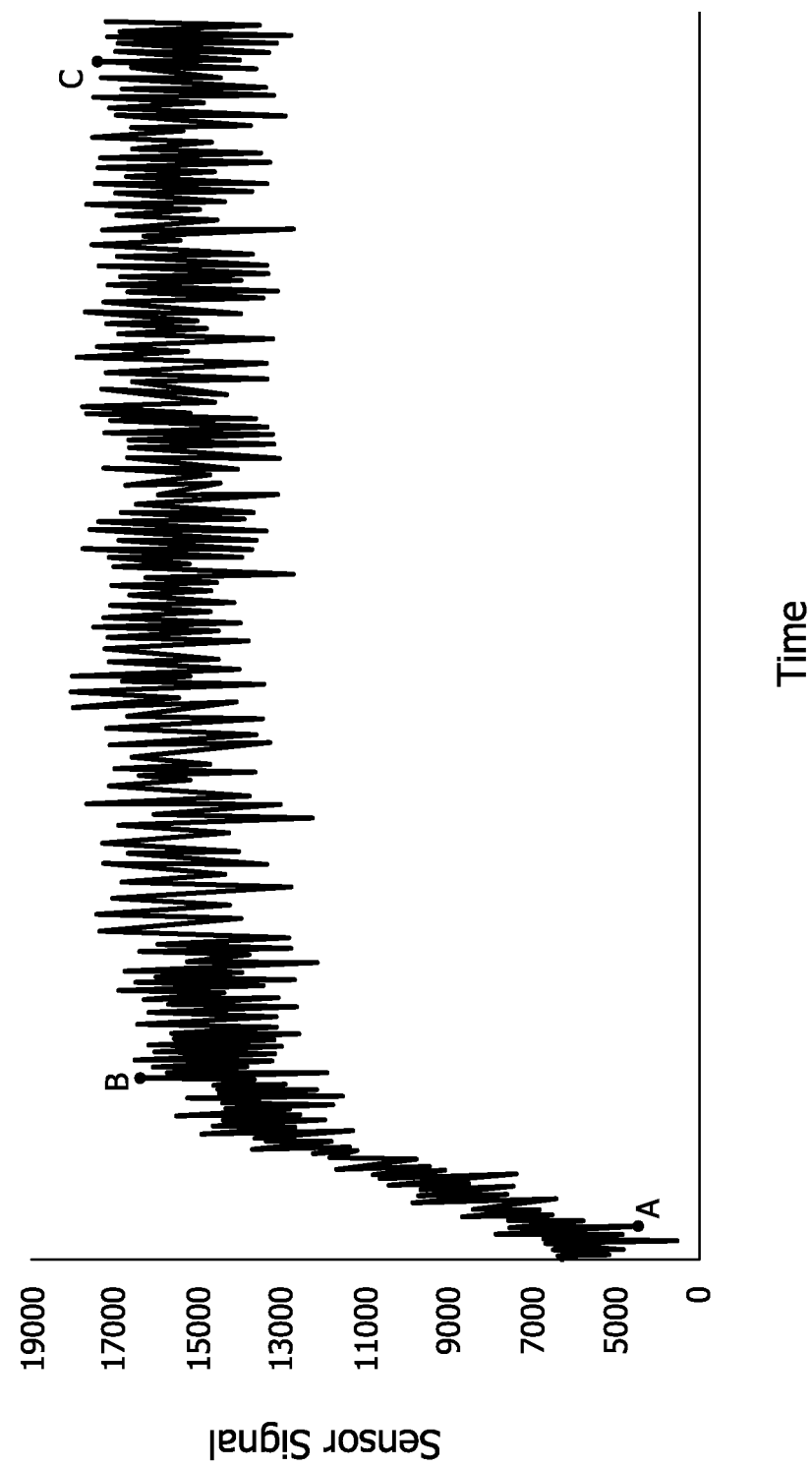
FIG. 8 is a graph illustrating signal strength over time for an occluded condition for a viscous fluid detected by the sensor of the flow monitoring system.
Figure 9:
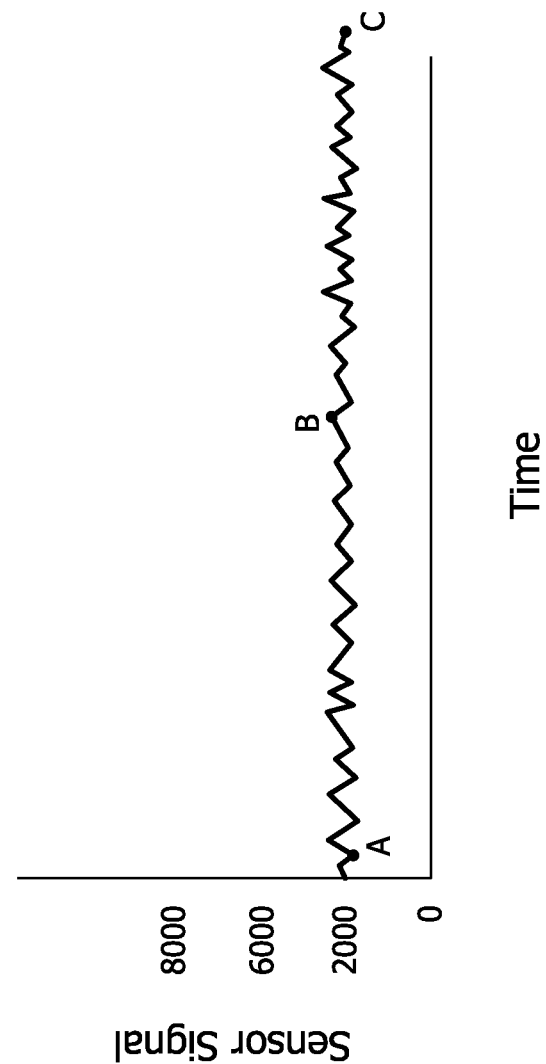
FIG. 9 is a graph illustrating signal strength over time for a non-occluded condition for a non-viscous fluid detected by the sensor of the flow monitoring system.

Referring to the flow chart in FIG. 5, the various decision points and steps executed by software subsystem 36 to perform test procedure A by flow monitoring system 12 are illustrated. Software subsystem 36 may direct flow control apparatus 10 to perform various operations related to detecting a flow conditions present in the feeding set 14. The graphs illustrated in FIGS. 6-9 provide examples of predetermined signal profiles that represent the relative signal strengths of the ultrasonic signal received by the receiver 52 for an occluded condition for a non-viscous fluid (FIG. 6), a non-occluded condition with a viscous fluid (FIG. 7), an occluded condition for a viscous fluid (FIG. 8), and a non-occluded condition for a non-viscous fluid (FIG. 9). These will be used to aid in explaining the operation of the flow monitoring system 12 in FIG. 6 to determine whether an occlusion or a normal flow condition exist in the tubing 16. It should be noted that while the graphs in FIGS. 6-9 depict examples of signal profiles, other profiles are envisioned for determining the various flow conditions.

Referring to FIG. 5, at 60 the software subsystem 36 may determine if the flow control apparatus 10 is in a non-operational state such that the rotor 26 is not rotating to deliver fluid through the feeding set 14. If the rotor 26 is not rotating, at 62, the microprocessor 31 may instruct the sensor 32 to transmit ultrasonic signals through the tubing 16 to provide the microprocessor with readings of the signals. At 64, the microprocessor 31 may record the baseline sensor signal reading. The microprocessor 31 may record readings from the sensor 32 in a database 66 (FIG. 4) (broadly, "memory"). A predetermined number of sensor signal readings may be stored in the database 66. The stored readings in the database 66 may be used by the microprocessor 31 to calculate a baseline signal just prior to activating the motor 28 to commence pumping. The signal readings can be averaged and or monitored to determine a minimal value of the signal readings to provide the baseline sensor signal. The baseline sensor signal can be updated as new readings from the sensor 32 are added to the database 66. This baseline sensor signal is exemplarily indicated as point A in FIGS. 6-9. However, in some cases, the baseline sensor signal can be a nominal sensor signal constituting an average of a predetermined number of discrete readings, e.g., in a range of from five to fifty consecutive sensor readings during periods without rotor operation.

At 68, the microprocessor 31 may then instruct the rotor 26 to begin rotating to deliver fluid through the feeding set 14. During a rotor turn operation, at 70, the microprocessor 31 may instruct the sensor 32 to transmit ultrasonic signals (US) through the tubing 16 to provide the microprocessor with readings of the signals. At 72, the microprocessor 31 may record the signal reading for a period of time. A predetermined number of sensor signal readings during the rotor turn may be stored in the database 66. The stored readings in the database 66 may be used by the microprocessor 31 to calculate a peak value of the signal readings. The signal readings can be recorded during an entire rotor operation or only during a portion (e.g., near the end) of the rotor operation. This peak sensor signal is indicated at B in FIGS. 6-9. Point B represents the point of maximal or peak internal pressure in the tubing 16. It is to be understood that in the described embodiment, the flow monitoring system 12, the software subsystem 36, pump electronics 74, the microprocessor 31 and database 66 may be broadly considered "a control circuit." These components may be individually considered "a control circuit." Moreover, other types of control circuits may be used within the scope of the present invention.

If during the rotor turn operation essentially no pressure is generated in the tubing 16, the amplitude of the signal will remain substantially constant. Thus, the amplitude will remain generally at point A. This may be indicative of a non-occluded normal flow condition for a non-viscous fluid. So points A and B would be generally the same for a non-occluded normal flow condition for a non-viscous fluid. This signal profile is shown in FIG. 9. If during the rotor turn operation pressure is generated in the tubing 16, the amplitude of the signal will increase. The amplitude may increase to point B. This pressure increase may be a result of an occlusion in the tubing if a non-viscous fluid is used (FIG. 6), a normal flow pressure increase from the use of a viscous fluid in the tubing (FIG. 7), or an occlusion in the tubing if a viscous fluid is used (FIG. 8).

At 75, the microprocessor 31 may compare the baseline sensor signal A with the peak sensor signal B. If the values are the same, the microprocessor 31 may indicate that a normal flow condition for a non-viscous fluid exists. However, if the peak sensor signal B is greater than baseline sensor signal A by more than a predetermined amount, the software subsystem 36 may consider an occlusion condition to be satisfied. For example, if the peak sensor signal B is more than 10% higher than baseline sensor signal A, then the software subsystem may conclude that one occlusion condition, e.g., a first occlusion condition, is satisfied. The amount by which the peak sensor signal B can exceed the baseline sensor signal A without satisfying the occlusion condition may be considered a pumping threshold. The pumping threshold may be other than described in this embodiment. The microprocessor 31 may not rely exclusively on this comparison because the indication of a flow abnormality may be a false positive if the fluid is viscous. In some cases, the peak signal is continually greater than the baseline signal during a peak predetermined period, then the first occlusion condition may be considered to be satisfied. The peak predetermined period may be in a range of from about five seconds to about sixty seconds.

At step 76 the microprocessor 31 may instruct the flow control apparatus 10 to stop rotation of the rotor 26 in a hold state. The hold state is a position of the rotor 26 that prevents pressure in the tubing 16 from being released from the tube. This may be accomplished by positioning the rotor 26 so that one of the rollers 30 deforms the tubing 16 to pinch off the tubing and block the flow of fluid in the tubing in a backflow direction opposite to the patient direction. After a predetermined period of time (i.e., a delay period), at 78, the microprocessor 31 may instruct the sensor 32 to transmit an ultrasonic signal through the tubing 16 to provide the microprocessor with a reading of the signal. At 80, a dissipation sensor signal reading in the hold state of the rotor 26 may be stored in the database 66. The dissipation sensor signal baseline is indicated at point C in FIGS. 6-9. The delay period can be in a range of from about 100 milliseconds to about one second.

If during the rotor turn operation no pressure is generated in the tubing 16, the amplitude of the signal will remain substantially constant. Thus, the amplitude will remain generally at point A. This is indicative of a non-occluded normal flow condition for a non-viscous fluid (FIG. 9). Points A, B, and C would be generally the same for a non-occluded normal flow condition for a non-viscous fluid. If pressure was generated in the tubing 16 during the rotor turn operation, increasing the signal amplitude to point B, in the hold state the amplitude of the signal may decrease such that point C is generally the same value as point A. This may be indicative of a normal flow condition for a viscous fluid (FIG. 7). The decrease in signal amplitude may be a result of the fluid continuing to flow in the patient direction after the rotor 26 has stopped turning. However, if pressure was generated during the operational state of the rotor, increasing the signal amplitude to peak sensor signal B, and during the post rotor turn operation the amplitude of the signal remained at the increased level such that dissipation sensor signal C is generally the same value as peak sensor signal B, this may be indicative of an abnormal flow condition (i.e., an occlusion). This condition is shown in FIG. 6 (non-viscous fluid) and FIG. 8 (viscous fluid). The maintained signal amplitude may be a result of the occlusion preventing the fluid from leaking from the feeding set 14 retaining the pressure in the tubing 16.

At 82, the microprocessor 31 may compare the baseline sensor signal A, to the dissipation sensor signal C, to provide an indication of the flow condition in the feeding set 14. In this instance, if the dissipation sensor signal C is substantially the same as the baseline sensor signal A, at 84, the microprocessor 31 may indicate that a normal flow condition exists. However, if the value for dissipation sensor signal C is higher than the value for baseline sensor signal A, the microprocessor 31 may indicate that an abnormal flow condition exists. For example, if the dissipation sensor signal C is more than 15% greater than the baseline sensor signal A, the software subsystem 36 may be programmed to conclude that another occlusion condition, e.g., a second occlusion condition, has been satisfied. The amount by which dissipation sensor signal C can exceed the baseline sensor signal A can be considered a baseline threshold. The baseline threshold can be other than described for this embodiment. In some cases, the second occlusion condition can be considered satisfied if the dissipation sensor signal remains greater than the baseline sensor signal, e.g., at or above the baseline threshold, for a predetermined dissipation period, e.g., in a range of from about five seconds to about sixty seconds. The baseline threshold can be in a range of from about ten percent to about thirty percent greater than the baseline sensor signal. Substantially the same in reference to comparing the various sensor signals includes compared values that are within or less than about five percent. However, in some cases, substantially the same can be considered as the nominal error associated with the measuring components of the flow control apparatus, e.g., within the operating tolerance of the sensor.

At 86, the microprocessor 31 may also compare the peak sensor signal B with the dissipation sensor signal C. If the peak sensor signal B is greater than dissipation sensor signal C by more than a predetermined amount, at 87, the software subsystem 36 may consider a third and final occlusion condition to be satisfied. For example, if dissipation sensor signal C is not less than the peak sensor signal B by 10% or more of the peak sensor signal, the software subsystem 36 may be programmed to conclude that an occlusion condition has been satisfied. The amount by which dissipation sensor signal C must be less than the peak sensor signal B to avoid satisfying the occlusion condition may be considered a dissipation threshold. The exact magnitude of the dissipation threshold can be other than described for this embodiment. In some cases, the third condition may be considered satisfied if the dissipation signal is not less than the peak sensor signal by at least ten percent for a predetermined period in a range of from about five seconds to about sixty seconds.

In the embodiment described herein, it may be that all three of the occlusion conditions described must be satisfied before the microprocessor 31 will cause an alarm 88 or other signal indicating the presence of an occlusion. It will be appreciated that if the peak sensor signal B exceeds baseline sensor signal A by more than the pumping threshold, it could be indicative of an occlusion, but also could be indicative of the behavior of a viscous fluid, such as shown in FIG. 7. In particular, by making sure that the peak sensor signal B exceeds the dissipation sensor signal C by more than the dissipation threshold and by also requiring dissipation sensor signal C to exceed baseline sensor signal A by more than a baseline threshold gives a high level of confidence that an occlusion is actually present. Moreover, the software subsystem 36 may be programmed to require all of the conditions be satisfied in more than one cycle of operation of the flow control apparatus before an occlusion alarm would be activated. For example, it may be required that all three occlusions conditions be satisfied in two consecutive cycles of operation of the flow control apparatus 10.

The microprocessor 31 may sound alarm 88 or stop operation of the apparatus 10 to repair or replace the feeding set 14 if an abnormal flow condition is declared. Preferably, alarm 88 may be audible, visual, tactile (e.g. vibratory) or any combination thereof. In one embodiment, a certain type of alarm 88 may represent a specific abnormal flow condition detected within the feeding set 14 and identifiable to the user by its own unique visual, audible and/or vibratory alarm. In one embodiment, the alarm 88 may cause a particular message to appear on the display 42. In addition or as an alternative, the alarm 88 may have different sounds that could indicate different types of flow conditions, such as a viscous fluid occlusion and a non-viscous fluid occlusion. These unique alarms 88 allow for flow monitoring system 12 to signal the presence of different abnormal flow conditions.

Figure 10:
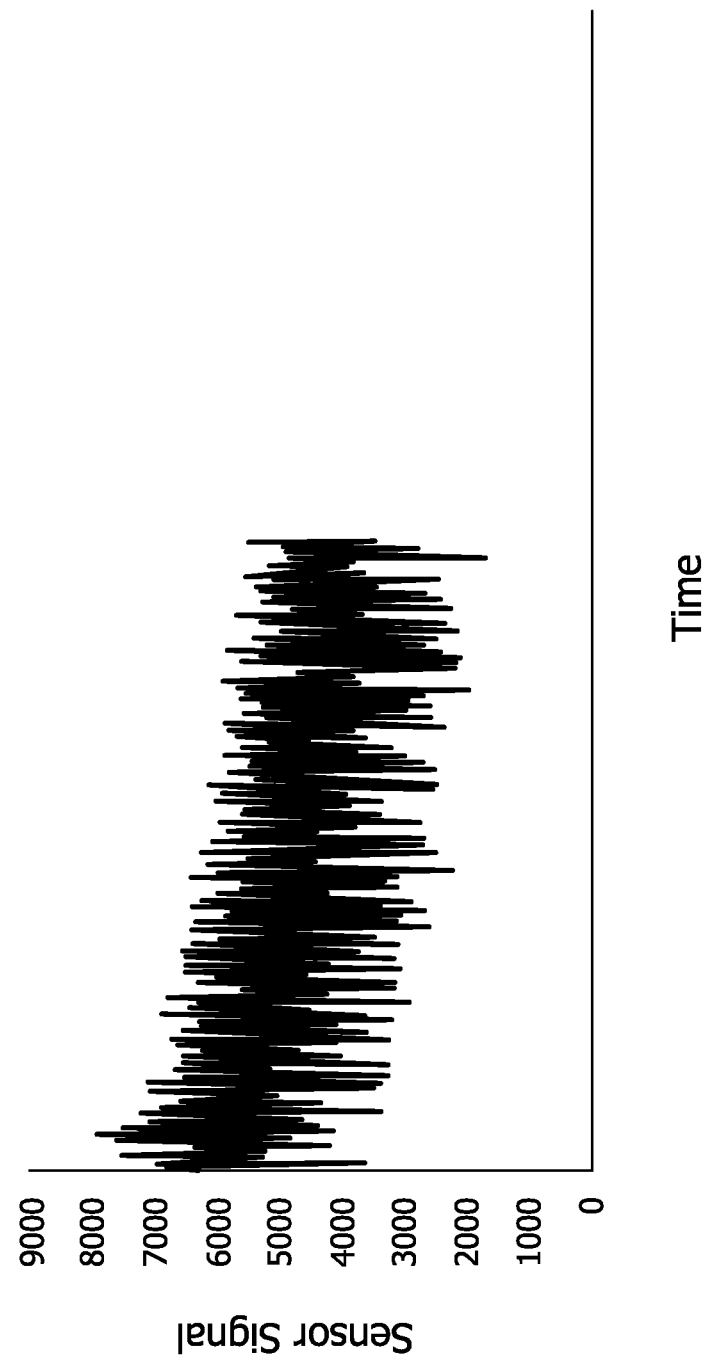
FIG. 10 is a graph illustrating signal strength over time for a post rotor turn period for a non-occluded condition for a viscous fluid detected by the sensor of the flow monitoring system.

At step 90, the microprocessor 31 may instruct the flow control apparatus 10 to restart rotation of the rotor 26 and stop the rotor in a reset state wherein the rollers 30 of the rotor 26 do not deform the tubing 16 in such a way as to prevent fluid flow through the tubing past the rotor in either direction. Even if an occlusion is present this allows pressure in the tubing 16 to decrease such as by flow of fluid in a backflow direction. Moreover, relieving pressure in this way avoids over-pressure damage to the feeding set 14 and flow control apparatus 10 if an occlusion is present. This decrease in pressure is illustrated in FIG. 10. By releasing the internal pressure in the tubing 16 generated from the previous rotor turns, subsequent rotor turn operations can begin with minimal to no internal pressure in the tubing. This allows the apparatus 10 to "self-calibrate" so the next sequence of rotor turns and signal readings can more accurately detect the flow condition in the feeding set 14. This is particularly beneficial where multiple cycles are being used to confirm an occlusion.

The process described above where the pressure in the tubing 16 is monitored when the apparatus 10 is non-operational (i.e., rotor 26 is not rotating) allows the apparatus to accurately detect a flow condition in the tubing 16 regardless of the viscosity of the fluid in the feeding set 14. By stopping the rotor 26 at various positions which retain and release pressure in the tubing 16, and detecting the pressure in the tubing at these locations, the apparatus 10 can accurately determine the flow condition in the feeding set 14 without regard for the viscosity of the fluid being used. Also, this process, and in particular step 90 where the rotor is rotated to the pressure release position, provides generally constant start conditions during the use of the apparatus 10 to determine the flow condition in the feeding set 14. This improves upon a system which relies exclusively on a pressure change when the rotor is rotated. In that instance, the apparatus would only have one chance to accurately detect an abnormal flow condition consistent with an occlusion because the pressure increase caused by the occlusion would result in the amplitude of the detection signal increasing to an elevated level and remaining at the elevated level as the rotor continues to be turned. Moreover, monitoring the pressure increase during a rotor turn may not accurately distinguish between normal and abnormal flow conditions, particularly when a viscous fluid is used. For these reasons, the apparatus 10 and process described above provide an improved device and method for detecting flow conditions of a feeding set mounted on the apparatus.

Embodiments of the invention may be described in the general context of computer-executable instructions, such as program modules, executed by one or more computers or other devices. The computer-executable instructions may be organized into one or more computer-executable components or modules including, but not limited to, routines, programs, objects, components, and data structures that perform particular tasks or implement particular abstract data types. Aspects of the invention may be implemented with any number and organization of such components or modules. For example, aspects of the invention are not limited to the specific computer-executable instructions or the specific components or modules illustrated in the figures and described herein. Other embodiments of the invention may include different computer-executable instructions or components having more or less functionality than illustrated and described.

Further, the order of execution or performance of the operations in embodiments of the invention illustrated and described herein is not essential, unless otherwise specified. That is, the operations may be performed in any order, unless otherwise specified, and embodiments of the invention may include additional or fewer operations than those disclosed herein. For example, it is contemplated that executing or performing a particular operation before, contemporaneously with, or after another operation is within the scope of aspects of the invention.

In operation, the microprocessor 31 executes computer-executable instructions such as those illustrated in the figures to implement aspects of the invention. Aspects of the invention may also be practiced in distributed computing environments where tasks are performed by remote processing devices linked through a communications network. In a distributed computing environment, program modules may be located in both local and remote computer storage media including memory storage devices.

Having described the invention in detail, it will be apparent that modifications and variations are possible without departing from the scope of the invention defined in the appended claims.

When introducing elements of the present invention or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the invention are achieved and other advantageous results attained.

As various changes could be made in the above constructions and methods without departing from the scope of the invention, it is intended that all matter contained in the above description and shown in the accompanying drawings shall be interpreted as illustrative and not in a limiting sense.

What is claimed is:

1. A flow control apparatus adapted to load a feeding set, said flow control apparatus comprising:
a housing capable of receiving at least a portion of the feeding set;
a pumping device for contacting the feeding set when the feeding set is received by the housing so the pumping device acts on the feeding set to produce fluid flow in the feeding set in a patient direction for delivery of fluid to a patient;
a sensor arranged with respect to the pumping device to produce a signal indicative of pressure in the feeding set when the feeding set is loaded on the apparatus for determining a flow condition in the feeding set; and
a control circuit in communication with the sensor for receiving the sensor signal from the sensor and in communication with the pumping device to control operation thereof, the control circuit being configured to operate the pumping device in an operational state in which the pumping device is adapted to contact the feeding set to produce a peristaltic pumping action of fluid in the patient direction through the feeding set, and in a hold state, after operation in the operational state, in which the pumping device is stopped and not moving so that the pumping device does not produce a peristaltic pumping action and blocks fluid flow in the feeding set in a backflow direction opposite to the patient direction, the control circuit receiving the sensor signal from the sensor when the pumping device is in the hold state and making a flow condition determination when the pumping device is in the hold state where the pumping device is stopped.

2. The flow control apparatus as set forth in claim 1 wherein the control circuit is configured to determine an occlusion is present in the feeding set based at least in part on a peak sensor signal and a dissipation sensor signal relative to a dissipation threshold amount.

3. The flow control apparatus as set forth in claim 2 wherein the control circuit comprises a memory and is configured to store the peak sensor signal from the operational state of the pumping device in the memory and configured to store the dissipation sensor signal from the hold state of the pumping device in the memory.

4. The flow control apparatus set forth in claim 3 wherein the control circuit is configured to delay for a predetermined period following onset of the hold state before acquiring the dissipation sensor signal to be stored in the memory.

5. The flow control apparatus as set forth in claim 4 wherein the control circuit is configured to compare the peak sensor signal with the dissipation sensor signal.

6. The flow control apparatus as set forth in claim 5 wherein the control circuit is configured to find that a first occlusion condition is satisfied if the dissipation sensor signal is not less than the peak sensor signal by more than the dissipation threshold amount.

7. The flow control apparatus as set forth in claim 5 wherein the control circuit is configured to compare the dissipation sensor signal with a baseline sensor signal taken in a reset state in which the pumping device does not produce a peristaltic pumping action and the pumping device is moved to a position in which the pumping device does not block the feeding set to permit fluid flow in the backflow direction and stored in the memory.

8. The flow control apparatus as set forth in claim 7 wherein the control circuit is configured to compare the baseline sensor signal with the peak sensor signal.

9. The flow control apparatus as set forth in claim 8 wherein the control circuit is configured to indicate that an occlusion is present in the feeding set if the following conditions are found: (1) the peak sensor signal is greater than the baseline sensor signal by more than a pumping threshold amount; (2) the dissipation sensor signal is greater than the baseline sensor signal by more than a baseline threshold amount, and (3) the dissipation sensor signal is not less than the peak sensor signal by more than the dissipation threshold amount.

10. The flow control apparatus as set forth in claim 9 wherein the control circuit is configured to indicate that an occlusion is present in the feeding set if said conditions are found in plural cycles of operation of the flow control apparatus where one cycle of operation includes the sequential operation of the pumping device in the operational state, the hold state and the reset state.

11. A method of operating a flow control apparatus including a pumping device for detecting occlusions in fluid flow in a pump set acted upon by the flow control apparatus, the method comprising:
operating the pumping device using a control circuit in an operational state to repeatedly deform the pump set for pumping fluid in the pump set;
halting operation of the pumping device using the control circuit;
moving the pumping device using the control circuit to a position in which the pumping device does not block the pump set to permit fluid flow in a backflow direction past the pumping device opposite to a pumping direction in which fluid in the pump set is pumped by the pumping device in the operational state and does not block the pump set to permit fluid flow in the pumping direction past the pumping device;
receiving a sensor signal from a sensor when the pumping device is in said position to determine presence of an occlusion in the pump set wherein the sensor signal indicates a pressure within the pump set.

12. The method as set forth in claim 11 further comprising:
operating the pumping device using the control circuit in a hold state in which the pumping device does not pump fluid in the pump set and blocks flow of fluid in the pump set in the backflow direction.

13. The method as set forth in claim 12 further comprising:
storing in a memory associated with the control circuit a baseline sensor signal from the sensor positioned to detect pressure in the pump set prior to initiation of operation of the pumping device by the control circuit to pump fluid in the pump set;
storing in the memory a peak sensor signal from the sensor acquired during operation of the pumping device in the operational state;
storing in the memory a dissipation sensor signal from the sensor acquired during operation of the pumping device in the hold state;
comparing using the control circuit the baseline sensor signal, the peak sensor signal and the dissipation sensor signal with each other;
determining with the control circuit the presence of an occlusion in the pump set only if a condition is satisfied in which the dissipation sensor signal is less than the peak sensor signal by less than a dissipation threshold amount.

14. The method set forth in claim 13 wherein determining with the control circuit the presence of an occlusion in the pump set further comprises determining if the following conditions are also met: (1) determining using the control circuit that the peak sensor signal is greater than the baseline sensor signal by more than a pumping threshold amount, and (2) determining using the control circuit that the dissipation sensor signal is greater than the baseline sensor signal by more than a baseline threshold amount.

15. A flow control apparatus adapted to load a feeding set, said flow control apparatus comprising:
a housing capable of receiving at least a portion of the feeding set;
a pumping device for contacting the feeding set when the feeding set is received by the housing so the pumping device acts on the feeding set to produce fluid flow in the feeding set for delivery of fluid in a patient direction to a patient;
a sensor arranged with respect to the pumping device to produce a signal indicative of pressure in the feeding set when the feeding set is loaded on the apparatus for determining a flow condition in the feeding set; and
a control circuit in communication with the sensor for receiving the sensor signal from the sensor indicative of the pressure in the feeding set and in communication with the pumping device to control operation thereof, the control circuit being configured to operate the pumping device in an operational state in which the pumping device is adapted to contact the feeding set to produce a peristaltic pumping action of fluid in the patient direction through the feeding set, and in a reset state in which the pumping device does not produce a peristaltic pumping action and the pumping device is moved to a position in which the pumping device does not block the feeding set to permit fluid flow in a backflow direction past the pumping device opposite to the patient direction thereby relieving any built up pressure in the feeding set downstream of the pumping device and does not block the feeding set to permit fluid flow in the patient direction past the pumping device, the control circuit receiving the sensor signal from the sensor when the pumping device is in the reset state.

16. The flow control apparatus as set forth in claim 15 wherein the control circuit is adapted to control the pumping device in the reset state, subsequent to the operational state, to move to a position that does not deform the feeding set so as to block flow of fluid through the feeding set.

17. The flow control apparatus of claim 16 wherein the pumping device comprises an actuator and pumping members operatively connected to the actuator for being moved by the actuator to repeatedly deform and relieve deformation of the feeding set for producing fluid flow in the feeding set in the patient direction, the control circuit in the reset state of the pumping device causing the pumping members to move to relieve deformation of the feeding set.

18. The flow control apparatus of claim 17 wherein the pumping device comprises a rotor operatively connected to the actuator for being driven in rotation by the actuator, the pumping members comprising rollers mounted on the rotor.

19. The flow control apparatus of claim 15 wherein the control circuit includes a memory and is configured to determine a first occlusion condition by comparing a baseline sensor signal acquired from the sensor prior to the operational state of the pumping device and stored in the memory with a peak sensor signal acquired during the reset state of the pumping device and stored in the memory.

20. The flow control apparatus of claim 19 wherein the control circuit is configured to operate the pumping device in a hold state subsequent to the operational state and prior to the reset state in which the pumping device does not produce a peristaltic pumping action and the pumping device is moved to a position in which the pumping device deforms the feeding set to block fluid flow in the backflow direction.

21. The flow control apparatus of claim 20 wherein the control circuit is configured to indicate that an occlusion is present in the feeding set only if said reset and hold states are found to indicate the presence of an occlusion in plural cycles of operation of the flow control apparatus where one cycle of operation includes the sequential operation of the pumping device in the operational state, the hold state and then the reset state.

22. The flow control apparatus of claim 15 wherein the sensor comprises an ultrasonic sensor including a receiver and an ultrasonic transmitter, the transmitter being configured to transmit an ultrasonic signal through a downstream side of the feeding set to the receiver for determining the downstream flow condition of the feeding set when the feeding set is loaded on the apparatus.

23. The flow control apparatus of claim 15 wherein the control circuit is configured to detect presence of an occlusion in the feeding set following sequential operation of the pumping device in the operational state, a hold state and the reset state.

24. The flow control apparatus as set forth in claim 1 wherein the hold state occurs prior to an occlusion determination.

* * * * *